United States Patent
Kitayama et al.

(10) Patent No.: US 7,387,668 B2
(45) Date of Patent: Jun. 17, 2008

(54) AZO COMPOUND, AQUEOUS DYE SOLUTIONS CONTAINING THE SAME, INKS AND USE THEREOF

(75) Inventors: Hirokazu Kitayama, Kita-ku (JP); Yasuo Shirasaki, Kita-ku (JP); Takahiko Matsui, Kita-ku (JP); Hiroaki Ohno, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/572,334

(22) PCT Filed: Sep. 29, 2004

(86) PCT No.: PCT/JP2004/014227

§ 371 (c)(1),
(2), (4) Date: May 25, 2006

(87) PCT Pub. No.: WO2005/033211

PCT Pub. Date: Apr. 14, 2005

(65) Prior Publication Data

US 2007/0119341 A1  May 31, 2007

(30) Foreign Application Priority Data

Oct. 1, 2003 (JP) .............................. 2003-343484

(51) Int. Cl.
C09D 11/00 (2006.01)
C09D 11/02 (2006.01)
C09B 56/04 (2006.01)
B41J 2/01 (2006.01)

(52) U.S. Cl. ............... 106/31.5; 106/31.47; 106/31.48; 106/31.49; 106/31.52; 534/691; 347/100

(58) Field of Classification Search ............ 106/31.47, 106/31.5, 31.52, 31.48, 31.49; 534/691; 347/100
See application file for complete search history.

(56) References Cited

U.S. PATENT DOCUMENTS

| | | | |
|---|---|---|---|
| 3,310,551 A | 3/1967 | McLeod et al. ............ 260/157 |
| 6,051,036 A | 4/2000 | Kusaki et al. .................. 8/494 |
| 7,056,374 B2* | 6/2006 | Kitayama et al. ........ 106/31.46 |
| 7,226,498 B2* | 6/2007 | Yamashita et al. ......... 106/31.5 |
| 2004/0099180 A1 | 5/2004 | Kitayama et al. ........ 106/31.46 |
| 2005/0131104 A1* | 6/2005 | Aikawa et al. ............. 523/160 |
| 2006/0005744 A1 | 1/2006 | Kitayama et al. ........ 106/31.48 |
| 2006/0119683 A1* | 6/2006 | Yoshizawa et al. ......... 347/100 |
| 2006/0119685 A1* | 6/2006 | Yamashita et al. .......... 347/100 |
| 2006/0124027 A1* | 6/2006 | Sato ........................ 106/31.6 |
| 2006/0139429 A1* | 6/2006 | Osumi et al. ............... 347/100 |
| 2007/0107627 A1* | 5/2007 | Negishi et al. .......... 106/31.27 |

FOREIGN PATENT DOCUMENTS

| | | |
|---|---|---|
| CN | 1057491 C | 10/2000 |
| DE | 1 932 826 | 1/1971 |
| DE | 1 544 347 | 9/1971 |
| EP | 0 605 730 | 7/1994 |
| EP | 1 378 549 | 1/2004 |
| FR | 1.392.965 | 4/1965 |
| GB | 1023799 | 3/1966 |
| JP | 42-3309 | 4/1963 |
| JP | 47-18548 | 9/1972 |
| JP | 57-195775 | 12/1982 |
| JP | 6-145569 | 5/1994 |
| JP | 2002-285022 | 10/2002 |
| JP | 2003-321627 | 11/2003 |
| WO | 94/02679 | 2/1994 |
| WO | 02/081580 | 10/2002 |
| WO | 2004/026964 | 4/2004 |

OTHER PUBLICATIONS

International Search Report dated Dec. 28, 2004.
European communication dated Nov. 22, 2007.
The Chinese communication dated Jul. 6, 2007, with English translation.

* cited by examiner

*Primary Examiner*—Helene Klemanski
(74) *Attorney, Agent, or Firm*—Nields & Lemack

(57) ABSTRACT

An azo compound which is reduced in the copper ion content and exhibits hue and clarity suitable for ink-jet recording and which can give records having excellent light fastness, water resistance, and moisture proofness, and such ozone resistance as to control the fading and the discoloration; and water-base yellow inks containing the same. In particular, the azo compound represented by the formula (12) having a content of impurity copper ions of 100 ppm or below or salts thereof, and inks containing the same (12)

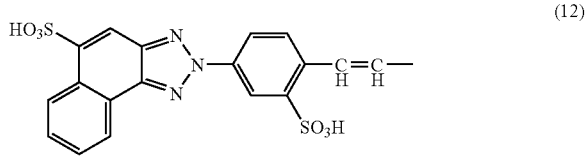

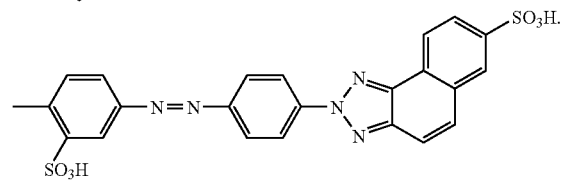

16 Claims, No Drawings

AZO COMPOUND, AQUEOUS DYE SOLUTIONS CONTAINING THE SAME, INKS AND USE THEREOF

TECHNICAL FIELD

The present invention relates to an azo compound and an ink, an aqueous dye solution, and an ink set using the azo compound, and an ink-jet recording method and a colored body using the ink or the ink set, and a method of manufacturing the azo compound.

BACKGROUND ART

Recently, image-recording materials have been developed primarily for forming color images. As such image recording materials, use may be frequently made of an ink-jet recording material, heat-sensitive transfer image recording material, xerographic recording material, transfer-system silver halide photosensitive material, printing ink, recording pen, and the like. Furthermore, color filters are used for liquid crystal displays (LCD) and plasma display panels (PDP) in displaying equipments and for electric parts such as charge-coupled devices (CCD) in photographing equipments. In these color image recording materials and color filters, full color images are reproduced or recorded by using three primary colors (dyes or pigments) of the additive color system and the subtractive color system. However, as a matter of fact, there are no dyes having an absorption property for realizing a preferable color reproduction range and usable under various use conditions. Therefore, improvement has been strongly desired.

In an ink-jet recording method, materials are not expensive, high-speed recording can be made with less noise, and color printing is easily made. For these reasons, the ink-jet recording method has rapidly come into wide use and is still undergoing development. In the ink-jet recording method, there are continuous and on-demand systems. In the continuous system, liquid droplets are continuously injected, whereas in the on-demand system, liquid droplets are injected in response to the image information signals. Liquid droplets are injected by the following systems. In a system, pressure is applied to a liquid by a piezo-electric element to inject liquid droplets. In another system, heat is applied to generate air bubbles in ink to inject liquid droplets. In still another system, an ultrasonic system is used. In still another system, an electrostatic system is used to inject liquid droplets by suctioning and injecting liquid droplets by electrostatic force. As ink suitable for ink-jet recording, mention may be made of aqueous ink, oily ink, and solid (molten state) ink, and the like.

Dye to be used in the ink suitable for ink-jet recording is required to have good solubility or dispersibility to a solvent, ability to attain high density recording, good hue, high resistance to light, heat and active gases (oxidative gas such as NOx and ozone, SOx, and others) in the environment, excellent resistance to water and chemical agents, good fixability to a recording medium with less bleeding, excellent storability as ink, no toxicity, and availability at low cost.

Furthermore, in recent years, owing to improvement of printing quality by an ink-jet printer, occasions for printing photographs have been increased. When an image of photographic quality is printed, a paper sheet called glossy paper, i.e., surface coated paper sheet, is used. However, such a surface coated paper has a problem called discoloration, which is caused by an active gas (in particular, ozone gas) in the environment. The degree of discoloration varies depending upon colors such as yellow, magenta, cyan, and black. Therefore, solving of problems raised after long time storage, that is, improving ozone resistance of each color as well as letting discoloration of colors due to ozone gas proceed at the same level have been important issues.

The dye skeleton of yellow used in aqueous ink-jet recording ink is typically an azo structure. As yellow, use may be made of C.I. Acid Yellow 17, C.I. Acid Yellow 23, C.I. Direct Yellow 86, C.I. Direct Yellow 132 and the like. Azo dyes presently on use, although some of them exhibit good hue and water resistance, are generally poor in light fastness. In particular, the level of light fastness of the yellow (azo) dye is lower than that of cyan dye represented by copper phthalocyanine dye. However, most of yellow dyes exhibit excellent ozone resistance. Because of this, discoloration of magenta, cyan, and black stands out in photographic printing. To overcome this problem, it has been desired to develop a yellow dye having an equivalent level of ozone resistance to other colors. Such a yellow dye has already been reported in the pamphlet of WO 02/081580A1 (Patent document 1). The method of synthesizing such a dye has been reported in Japanese Patent Publication (KOKOKU) No. 47-18548 (Patent document 2). However, the compound synthesized by the method reported in the publication contains a large amount of copper ions since a large amount of copper sulfate is used in a triazolization reaction. On the other hand, Japanese Patent Application Laying-Open (KOKAI) No. 2000-355665 (Patent document 4) has reported that the concentration of free copper ions contained in ink-jet recording ink is desirably reduced to 10 ppm or less. For a compound synthesized by the method described in Patent document 2 to satisfy the conditions of Patent document 4, copper ions must be removed. To do this, additional processes such as precipitation under acidic condition, salting-out, and treatment with an ion exchange resin are additionally required. This is unfavorable in manufacturing.

LIST OF DOCUMENTS

[Patent document 1]: WO 02/081580A1
[Patent document 2]: Japanese Patent Publication (KOKOKU) No. 47-18548
[Patent document 3]: Japanese Patent Publication (KOKOKU) No. 55-11708
[Patent document 4]: Japanese Patent Application Laying-Open (KOKAI) No. 2000-355665

DISCLOSURE OF THE INVENTION

It is an object of the present invention to provide an azo compound having suitable hue and clarity for ink-jet printing, excellent storage stability, capable of providing a printed matter excellent in fastness including light fastness and moisture resistance, and having ozone resistance controllable at equivalent levels to magenta, cyan, and black. The present invention is further directed to providing ink containing such an azo compound, and an ink set containing the ink, an ink-jet recording method using the ink and ink set, a colored body, and a method of producing such an azo compound.

The present inventors have intensively investigated with a view to attaining the object and then achieved the present invention.

More specifically, according to the present invention, there is provided (1) An azo compound represented by the following formula (12) having a content of copper ions as impurity of 100 ppm or less, or a salt thereof;

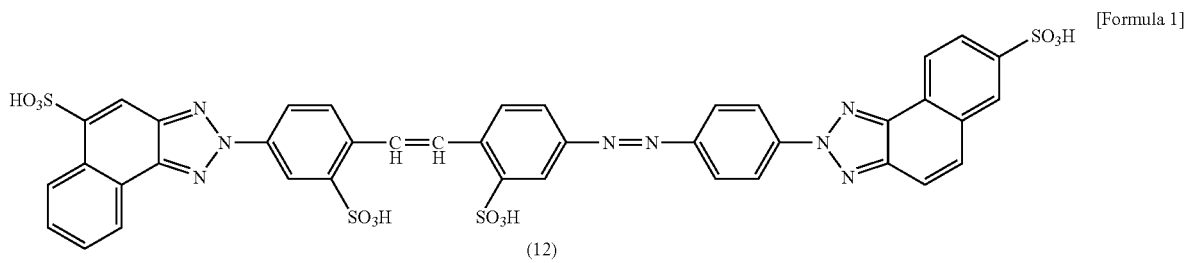

(2) An aqueous dye solution characterized by comprising the azo compound represented by the formula (12) or a salt thereof according to item (1) in an amount of 10% by mass or more and having pH of 6 to 11;

(3) The aqueous dye solution according to item (2), in which the content of inorganic anions is 1% by mass or less;

(4) Ink characterized by comprising the azo compound represented by the formula (12) or a salt thereof according to item (1) as a dye component;

(5) Ink characterized by comprising the azo compound represented by the formula (12) or a salt thereof according to item (1) and an azo yellow dye (B);

(6) The ink according to item (5), in which the azo yellow dye (B) is a compound represented by the following general formula (2), (3) or (4):

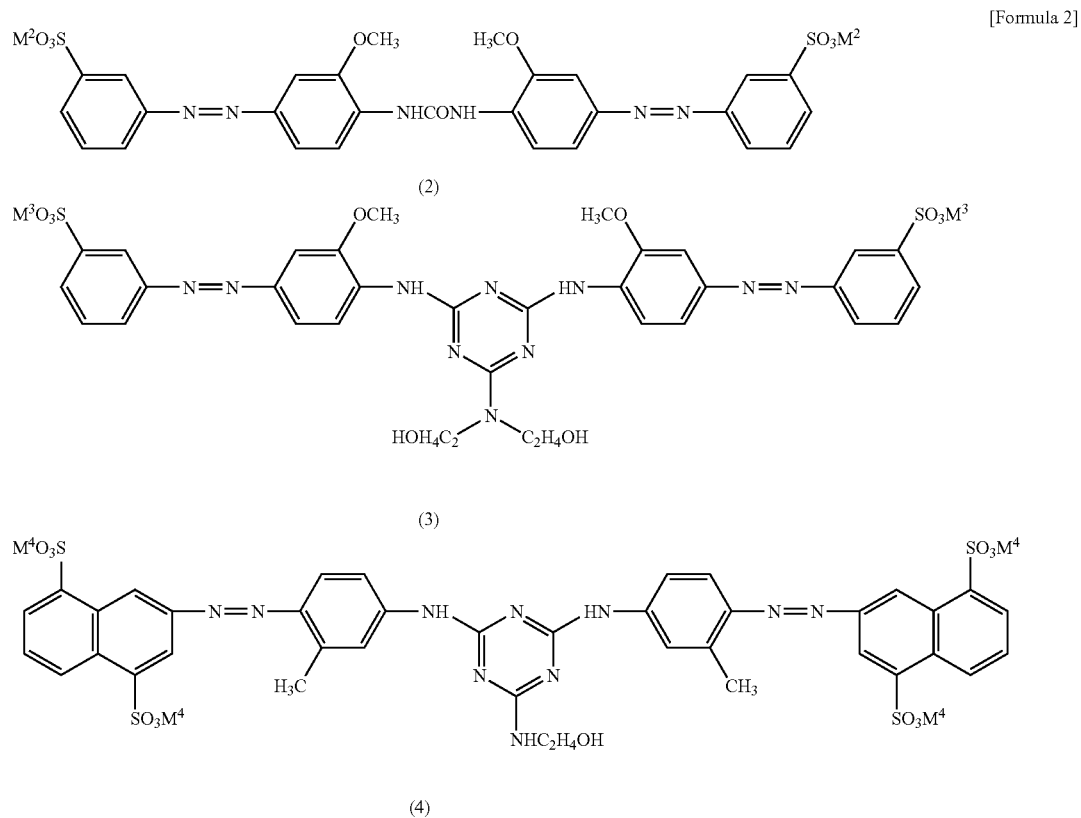

wherein $M^2$ to $M^4$ each independently represent a hydrogen atom, alkali metal, alkaline earth metal, cation of an organic amine, or ammonium ion;

(7) The ink according to item (6), in which the azo yellow dye (B) is composed of not less than two compounds represented by the general formulas (2) to (4);

(8) The ink according to any one of items (4) to (7), comprising water and a water-soluble organic solvent;

(9) The ink according to any one of items (4) to (8) for ink-jet recording;

(10) An ink set characterized by comprising the ink according to any one of items (4) to (9) as yellow ink, at least one water-soluble anthrapyridone dye as magenta ink, and at least one water-soluble copper phthalocyanine dye as cyan ink;

(11) An ink-jet recording method for recording an image on a recording medium by injecting ink droplets in response to recording signals, characterized in that the ink according to any one of items (4) to (9) or the ink set according to item (10) is used;

(12) The ink-jet recording method according to item (11), in which the recording medium is an information transmission sheet;

(13) The ink-jet recording method according to item (12), in which the information transmission sheet is a surface-coated sheet and has an ink-image receiving layer containing white inorganic pigment particles on a substrate;

(14) An ink container characterized by comprising the ink according to any one of items (4) to (9) or ink contained in the ink set according to item (10);

(15) An ink-jet printer comprising the ink container according to item (14);

(16) A colored body characterized by being colored by the ink according to any one of items (4) to (9) or the ink set according to item (10); and

(17) A method of producing a compound represented by the general formula (1), characterized by comprising reacting a disazo compound represented by the following general formula (5):

wherein m and n each independently represent 1 or 2; and $M^1$ represents a hydrogen atom, alkali metal, alkaline earth metal, cation of an organic amine, or ammonium ion, with sodium hypochlorite in water.

BEST MODE FOR CARRYING OUT THE INVENTION

The present invention will be explained in detail below.

A method of producing a compound represented by the general formula (1) and a salt thereof will be explained. First, a disazo compound represented by the general formula (5) is synthesized in accordance with the method described in Patent document 2 and the like. Note that a triazole ring in the formula is known to have tautomers.

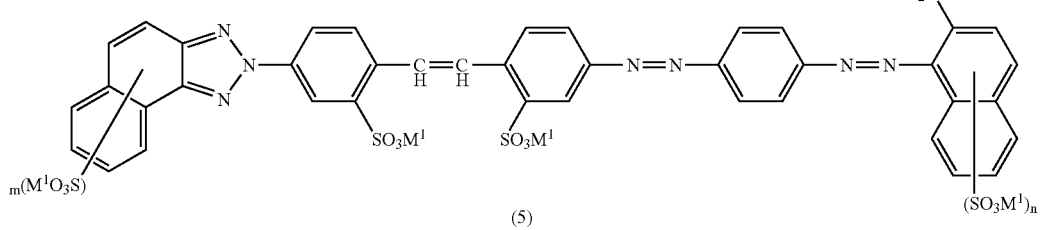

(5)

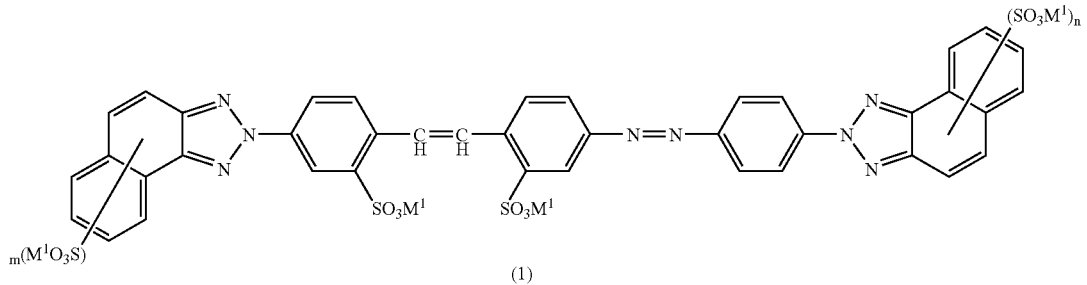

(1)

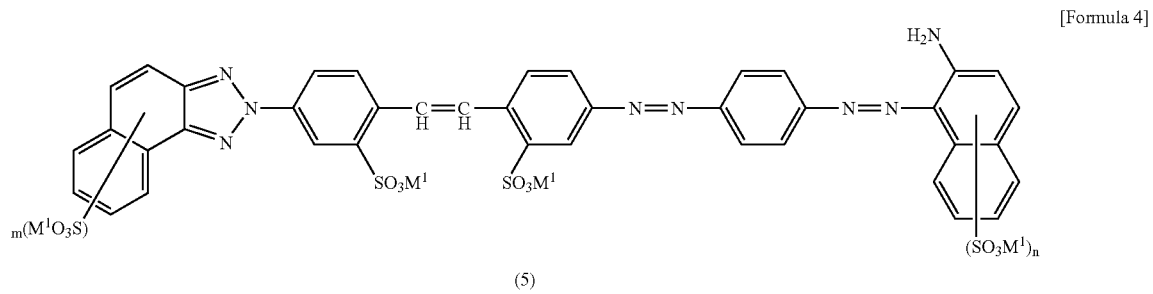

[Formula 4]

(5)

Subsequently, a disazo compound represented by the general formula (5) is reacted with sodium hypochlorite in water generally in the conditions: pH 8-13 and a temperature of 30 to 100° C., for 0.1 to 12 hours to obtain a triazolized compound represented by the general formula (1).

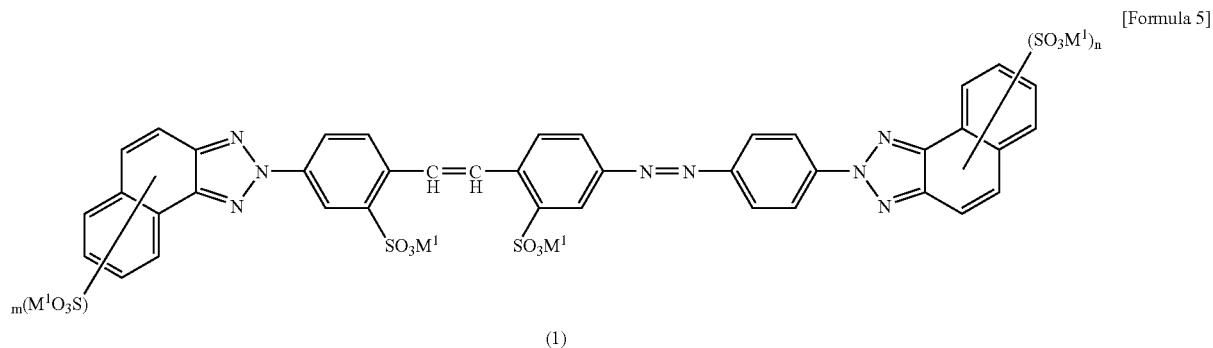

[Formula 5]

(1)

In the triazolization reaction for obtaining a compound represented by the general formula (1) from a compound represented by the general formula (5), a large amount of copper sulfate is used in the method described in Patent document 2. As a result, a large amount of copper ions remains in the compound represented by the general formula (1).

However, in the method of the present invention mentioned above to obtain the compound of the general formula (1), the triazolization is carried out by a reaction with sodium hypochlorite. Therefore, copper ions would not be mixed except for the case where they are present in starting materials as impurities. For this reason, the compound of the general formula (1) obtained by the method of the present invention is suitable for ink-jet application. Of the compounds represented by the general formula (1) with reduced copper-ion content, use may be particularly preferably made of the azo compound represented by the formula (12) and a salt thereof having a content of copper ions as impurity of 100 ppm or less.

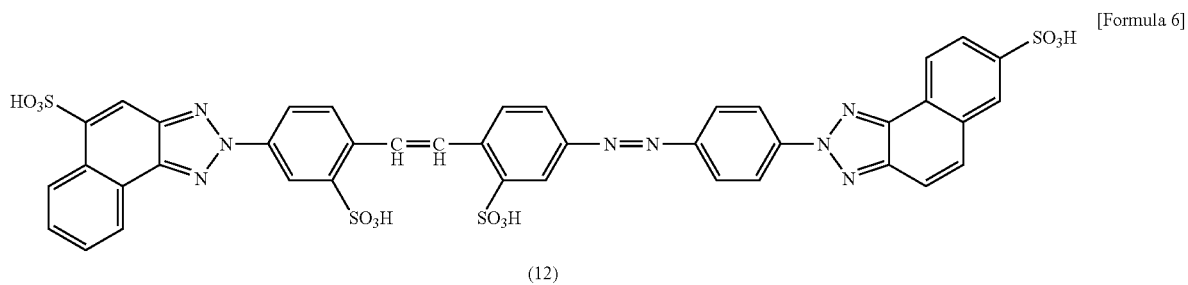

[Formula 6]

(12)

In the present invention, the compound represented by the formula (12) or a salt thereof may be used in combination with an azo yellow dye (B). As the azo yellow dye to be used, mention may be made of an azo yellow dye having its absorption peak in the range of 350 nm to 450 nm in an absorption spectrum determined by a spectrophotometer under measurement conditions: D65 light source, a visual field of 2°, and the optical path length of transmission light is 10 mm, wherein the pH of the dye is adjusted to 7 to 8 with ion exchanged water, and the peak absorbance is adjusted so as to fall within the range of 1 to 2 Abs in the wavelength range of 300 nm to 800 nm. Examples of such azo yellow dye include compounds represented by the general formulas (2) to (4) and those expressed by color indexes including C.I. Direct Yellow 27, C.I. Direct Yellow 28, C.I. Direct Yellow 33, C.I. Direct Yellow 34, C.I. Direct Yellow 39, C.I. Direct Yellow 44, C.I. Direct Yellow 87, C.I. Direct Yellow 100, C.I. Direct Yellow 120, C.I. Direct Yellow 173, C.I. Acid Yellow 3, C.I. Acid Yellow 17, C.I. Acid Yellow 19, C.I. Acid Yellow 23, C.I. Acid Yellow 25, C.I. Acid Yellow 29, C.I. Acid Yellow 38, C.I. Acid Yellow 42, C.I. Acid Yellow 49, C.I. Acid Yellow 59, C.I. Acid Yellow 61, and C.I. Acid Yellow 72. Of them, compounds represented by the general formulas (2) to (4) are preferably used.

lamine, monoethanolamine, diethanolamine, triethanolamine, monoisopropanolamine, diisopropanolamine, and triisopropanolamine. Examples of preferable $M^1$ to $M^4$ include a hydrogen atom; alkali metals such as sodium, potassium, and lithium; ammonium ion and alkanolamine ions such as monoethanolamine ion, diethanolamine ion, triethanolamine ion, monoisopropanolamine ion, diisopropanolamine ion, and triisopropanolamine ion. As a salt of the azo compound of the formula (12), mention may be made of salts of the aforementioned compounds.

These salts are produced by adding sodium chloride, for example, in the case of a sodium salt, to a reaction solution, thereby salting out and filtering the sodium salt. Furthermore, the sodium salt is dissolved in water and acid is added to the resultant solution, thereby precipitating crystals in

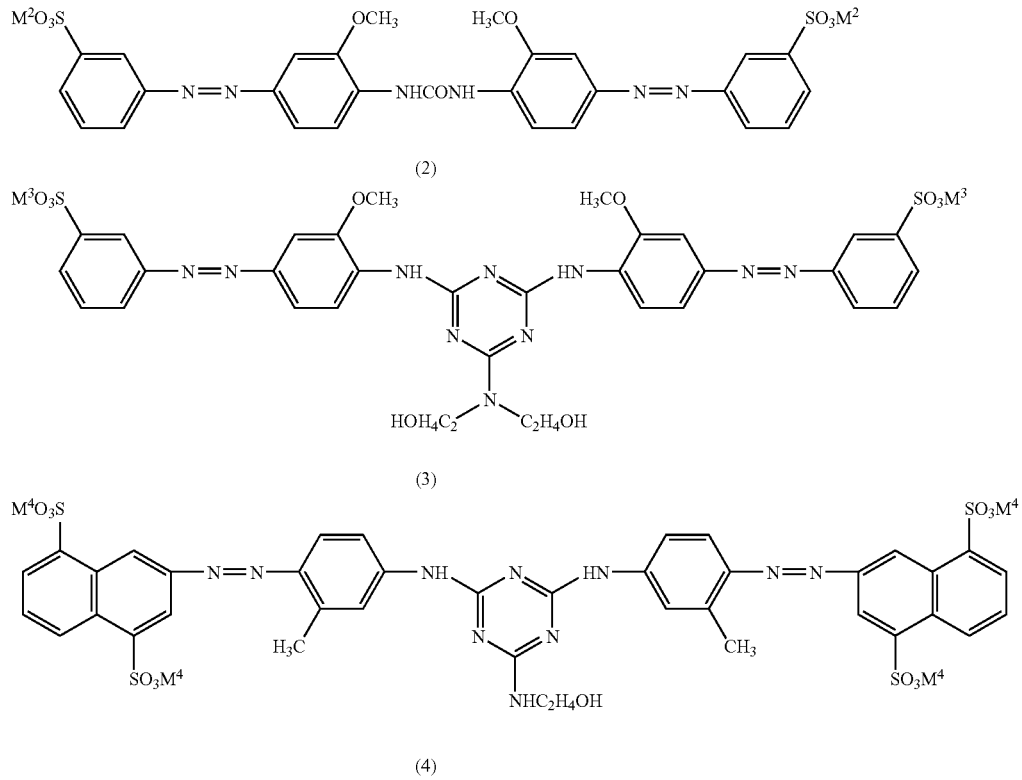

[Formula 7]

The number of dye components to be used in combination with the compound represented by the formula (12) may be two or more. The standard mixing ratio (by mass) of the compound of the formula (12) and other dye components is from 99:1 to 1:99, and preferably 90:10 to 10:90.

A compound represented by the general formula (2) is known as C.I. Direct Yellow 132 and a compound of the general formula (4) as C.I. Direct Yellow 86, respectively. They can be readily obtained. A compound represented by the general formula (3) can be produced, for example, by the method described in Patent document 3.

In the general formulas (1) to (5), $M^1$ to $M^4$ each are a hydrogen atom, alkali metal, alkaline earth metal, cation of an organic amine, or ammonium ion. Examples of the alkali metal include sodium, potassium and lithium. Examples of the alkaline earth metal include calcium and magnesium. Examples of the organic amine include methylamine, ethyacidic conditions. Thereafter, crystals are filtered to form a cake of a dye present in the form of free acid. Subsequently, the free-acid form dye cake is dissolved or suspended in water and then, a base corresponding to a desired salt, for example, an amine, or an alkali metal compound except for Na compound, etc. is added and dissolved. In this manner, a solution of each salt can be obtained. The solution is subjected to precipitation, filtration, and drying in accordance with a customary method to obtain salts except for a sodium salt.

The yellow ink of the present invention contains the azo compound of the formula (12) or a salt thereof produced by the aforementioned method, and is preferably prepared by using water as a medium. When the ink is used as ink-jet recording ink, the content of inorganic anions such as $Cl^-$ and $SO_4^{2-}$ in the compound is preferably low. The standard content of inorganic anions, as expressed by the total content of Cl⁻ and $SO_4^{2-}$, is not more than 5% by mass, preferably not more than 3% by mass, and further preferably, not more than 1% by mass, in other words, not more than 1% by mass in ink. To obtain the compound of the present invention reduced in content of Cl⁻ and $SO_4^{2-}$, desalting treatment may be performed, for example, by a method using a general reverse osmotic membrane or by a method in which a dried product or a wet cake of the compound of the present invention is stirred in a solvent mixture of alcohol and water, filtered and dried. The alcohol to be used herein may be a lower alcohol having 1 to 4 carbon atoms, preferably an alcohol having 1 to 3 carbon atoms, and more preferably, methanol, ethanol, or 2-propanol. Furthermore, when the compound of the present invention is desalted with an alcohol, use may be made of a method in which the solution is heated to near a boiling temperature of the alcohol to be used and then cooled. The contents of Cl⁻ and $SO_4^{2-}$ can be measured by, for example, ion chromatography.

When the yellow ink of the present invention is used as ink-jet recording ink, the content of metal ions as impurity in the compound is preferably low. More specifically, as described above, the content of copper ions is 100 ppm or less, and preferably 10 ppm or less. The content of heavy metal ions except for copper ions, such as zinc and iron ions, or metal ions such as calcium and silica, is preferably low. The standard contents of heavy metal (ions) such as zinc and iron and metal (cations) such as calcium and silica in a dried and purified product of the compound are about 500 ppm or less for each. The contents of heavy metal (ions) and metal (cations) are measured by ion chromatography, atomic absorption method or Inductively Coupled Plasma (ICP) emission spectroscopic analysis.

The ink of the present invention is preferably prepared using water as a medium. In the ink of the present invention, the azo compound of the formula (12) or a salt thereof, which is obtained in the aforementioned manner so as to satisfy the aforementioned conditions, is generally contained in an amount of 0.3 to 10% by mass.

In the ink of the present invention, if necessary, a water soluble organic solvent may further be contained within the range having no adverse effect upon the effects of the present invention. The water soluble organic solvent may be used as a dye dissolving agent, dryness inhibitor (moisturizing agent), viscosity adjuster, permeation accelerator, surface tension adjuster, antifoaming agent and the like. As other agents for use in preparing ink, mention may be made of known additives such as an antiseptic/antifungal agent, pH adjuster, chelating agent, anti-rusting agent, UV absorber, viscosity adjuster, dye dissolving agent, anti-discoloration agent, emulsion stabilizer, surface tension adjuster, antifoaming agent, dispersant, and dispersion stabilizer. The content of the water soluble organic solvent is 0 to 60% by mass, and preferably 10 to 50% by mass. The content of said agents for use in preparing ink is 0 to 20% by mass, and preferably 0 to 15% by mass.

Examples of the water soluble organic solvent to be used in the present invention include C1 to C4 alkanols such as methanol, ethanol, n-propanol, isopropanol, n-butanol, isobutanol, secondary butanol, and tertiary butanol; carboxylic acid amides such as N,N-dimethylformamide, and N,N-dimethylacetamide; heterocyclic ketones such as 2-pyrrolidone, N-methyl-2-pyrrolidone, 1,3-dimethylimidazolidin-2-one, and 1,3-dimethylhexahydropyrimid-2-one; ketones or ketoalcohols such as acetone, methylethyl ketone, and 2-methyl-2-hydroxypentan-4-one; cyclic ethers such as tetrahydrofuran, and dioxane; monomers, oligomers, polyalkylene glycols having a C2 to C6 alkylene unit or thioglycols, such as ethylene glycol, 1,2-propylene glycol, 1,3-propylene glycol, 1,2-butylene glycol, 1,4-butylene glycol, 1,6-hexylene glycol, diethylene glycol, triethylene glycol, tetraethylene glycol, dipropylene glycol, thiodiglycol, polyethylene glycol, and polypropylene glycol; polyols (triols) such as glycerol, and hexane-1,2,6-triol; C1-C4 alkyl ethers of a polyalcohol, such as ethylene glycol monomethyl ether, ethylene glycol monoethyl ether, diethylene glycol monomethyl ether, diethylene glycol monoethyl ether, triethylene glycol monomethyl ether, and triethylene glycol monoethyl ether; γ-butyrolactone; and dimethylsulfoxide.

Of the water soluble organic solvents mentioned above, use may be preferably made of isopropanol, glycerol, ethylene glycol, diethylene glycol, triethylene glycol, dipropylene glycol, 2-pyrrolidone, and N-methyl-2-pyrrolidone; and more preferably made of isopropanol, glycerol, diethylene glycol, and 2-pyrrolidone. These water soluble organic solvents may be used singly or in the form of a mixture.

Examples of the antiseptic/antifungal agent include compounds of organic sulfur type, organic nitrogen and sulfur type, organic halogen type, haloallyl sulfone type, iodopropargyl type, N-haloalkylthio type, benzothiazole type, nitrile type, pyridine type, 8-oxyquinoline type, benzothiazole type, isothiazoline type, dithiol type, pyridine oxide type, nitropropane type, organotin type, phenol type, quaternary ammonium salt type, triazine type, thiadiazine type, anilide type, adamantane type, dithiocarbamate type, brominated indanone type, benzyl bromoacetate type and inorganic salt type. Examples of the organic halogen type compound include sodium pentachlorophenol. Examples of the pyridine oxide type compounds include sodium 2-pyridinethiol-1-oxide. Examples of the inorganic salt type compounds include anhydrous sodium acetate. Examples of the isothiazoline type compounds include 1,2-benzoisothiazolin-3-one, 2-n-octyl-4-isothiazolin-3-one, 5-chloro-2-methyl-4-isothiazolin-3-one, 5-chloro-2-methyl-4-isothiazolin-3-one-magnesium chloride, 5-chloro-2-methyl-4-isothiazolin-3-one calcium chloride, and 2-methyl-4-isothiazolin-3-one calcium chloride. As other antiseptic/antifungal agents, mention may be made of sodium sorbate, and sodium benzoate (e.g., Proxel GXL(S) and Proxel XL-2(S) manufactured by Avecia).

As the pH adjuster, any substance may be used as long as it can control pH of ink within the range of 6 to 11 to improve the storage stability of ink. Examples of the pH adjuster include alkanolamines such as diethanolamine and triethanolamine; alkali metal hydroxides such as lithium hydroxide, sodium hydroxide, and potassium hydroxide; ammonium hydroxide; and alkali metal carbonates such as lithium carbonate, sodium carbonate, and potassium carbonate.

Examples of the chelating agent include sodium ethylenediaminetetraacetate, sodium nitrilotriacetate, sodium hydroxyethylethylenediaminetriacetate, sodium diethylenetriaminepentaacetate, and sodium uramil diacetate. Examples of the anti-rusting agent include acidic sulfites, sodium thiosulfate, ammonium thioglycolate, diisopropylammonium nitrite, pentaerythritol tetranitrate, and dicyclohexylammonium nitrite.

Examples of the UV absorber include benzophenone type compounds, benzotriazole type compounds, cinnamic acid type compounds, triazine type compounds, and stilbene type compounds. Other than these, use may also be made of compounds represented by a benzoxazole type compound called a fluorescent whitener, absorbing UV rays and emitting fluorescence.

Examples of the viscosity adjuster include water-soluble organic solvents and water-soluble polymer compounds such as polyvinyl alcohol, cellulose derivatives, polyamines, and polyimines.

Examples of a dye dissolving agent include urea, ε-caprolactam, and ethylene carbonate.

The anti-discoloration agent is used for improving the storage stability of images. As the anti-discoloration agent, use may be made of various anti-discoloration agent of organic type and metal complex type. Examples of the organic anti-discoloration agent include hydroquinones, alkoxyphenols, dialkoxyphenols, phenols, anilines, amines, indanes, chromanes, alkoxyanilines, and heterocycles. Examples of the metal complex type include nickel complexes and zinc complexes.

As the surface tension adjuster, mention may be made of surfactants including anionic surfactants, amphoteric surfactants, cationic surfactants and nonionic surfactants. Examples of the anionic surfactants include alkyl sulfocarboxylate salts, α-olefin sulfonate salts, polyoxyethylene alkyl ether acetate salts, N-acyl amino acids and salts thereof, N-acylmethyltaurine salts, alkyl sulfate salt, polyoxyalkyl ether sulfate salt, alkyl sulfate salt, polyoxyethylenealkyl ether phosphate salt, rosined soap, castor oil sulfate salt, lauryl alcohol sulfate salt, alkyl phenol phosphate ester, alkyl phosphate ester, alkylallyl surfonate salt, diethylsulfosuccinate salt, diethylhexylsulfosuccinate salt and dioctylsulfosuccinate salt. Examples of the cationic surfactant include 2-vinylpyridine derivatives and poly-4-vinylpyridine derivatives. Examples of the amphoteric surfactant include lauryldimethyl aminoacetic acid betaine, 2-alkyl-N-carboxymethyl-N-hydroxyethylimidazolinium betaine, propyldimethylaminoacetic acid betaine, palm oil fatty acid amide, polyoctylpolyaminoethylglycine, and other imidazoline derivatives. Examples of the nonionic surfactant include ethers such as polyoxyalkylene alkyl ethers, for example, polyoxyethylene nonyl phenyl ether, polyoxyethylene octyl phenyl ether, polyoxyethylene dodecyl phenyl ether, polyoxyethylene octyl phenyl ether, polyoxyethylene oleyl ether, polyoxyethylene lauryl ether, and polyoxyethylene alkyl ether; esters such as polyoxyethylene oleic acid, polyoxyethylene oleate, polyoxyethylene distearate, sorbitan laurate, sorbitan monostearate, sorbitan monooleate, sorbitan sesquioleate, polyoxyethylene monooleate, and polyoxyethylene stearate; and acetylene glycols such as 2,4,7,9-tetramethyl-5-decyne-4,7-diol, 3,6-dimethyl-4-octyne-3,6-diol, and 3,5-dimethyl-1-hexyne-3-ol (for example, Sarfinol® 104E, 104PG50, 82, 465, and Olfin STG manufactured by Nissin Chemical Industry Co., Ltd.). These surface tension adjuster may be used singly or in the form of a mixture. Note that the surface tension of the ink of the present invention is generally 25 to 70 mN/m, preferably, 25 to 60 mN/m. The viscosity of the ink of the present invention is preferably adjusted to 30 mPa·s or less and more preferably 20 mPa·s or less.

As the antiforming agent, fluorine compounds and silicone compounds may be used, as needed.

The order in which respective agents are dissolved in producing the ink of the present invention is not particularly limited. Water for use in preparing the ink is preferably reduced in content of impurities. Ion exchanged water or distilled water are preferably used. Furthermore, impurities may be removed from the ink obtained by subjecting it to microfiltration using a membrane filter and the like. Microfiltration is preferably performed when the ink is used as one for ink-jet printer. The pore diameter of the filter for use in microfiltration is generally 1 μm to 0.1 μm, and preferably 0.8 μm to 0.2 μm.

The ink of the present invention may be used for forming not only single color images but also full color images. To form full color images, the ink of the present invention may be used as one of ink colors in an ink set containing also magenta ink, cyan ink and black ink. To form more precise images, it may be used as one of ink colors in an ink set containing also light magenta ink, light cyan ink, blue ink, green ink, orange ink, dark yellow ink, and gray ink.

As a dye that can be applied as magenta ink, various types of magenta dyes may be used. For example, use may be made of aryl or heteroazo dyes having a phenol type residue, naphthol type residue, aniline type residue as a coupler agent; azomethine dyes having a kind of pyrazolone and pyrazolotriazole as a coupler agent; methine dyes such as an arylidene dye, styryl dye, merocyanine dye, cyanine dye, and oxonol dye; carbonium dyes such as a diphenylmethane dye, triphenylmethane dye, and xanthene dye; quinone dyes such as a naphthoquinone dye, anthraquinone dye, and anthrapyridone dyes; and condensed polycyclic dyes such as a dioxazine dye. Preferably, anthraxpyridone dyes are used.

As a dye that can be applied as cyan ink, various types of cyan dyes may be used. For example, use may be made of a phthalocyanine dye; methine dyes such as arylidene dye, styryl dye, merocyanine dye, cyanine dye, and oxonol dye; carbonium dyes such as diphenylmethane dye, triphenylmethane dye, and xanthene dye; and quinone dyes such as naphthoquinone dye and anthraquinone dye. Preferably, phthalocyanine dye and more preferably copper phthalocyanine dye is used.

Each of the dyes mentioned above may emit colors such as yellow, magenta, and cyan only after dissociating part of a chromophore. In this case, as a counter cation, use may be made of an inorganic cation such as an alkali metal and ammonium, and an organic cation such as pyridinium, and quaternary ammonium, and furthermore, a polymer cation containing these within the polymer structure. As a dye that can be applied as a black dye, use may be made of disazo, trisazo, and tetraazo dyes. Other than these, dispersed carbon black may be mentioned.

The ink of the present invention is applicable to printing, copying, marking, writing, drafting, stamping or recording process, in particular, ink-jet printing process.

In the ink-jet recording method of the present invention, an image is formed on a recording medium (image receiving material) such as a general paper sheet, resin coated sheet, ink-jet-specific paper sheet, glossy sheet, glossy film, electrophotography common use paper, fiber and fabric (cellulose, nylon, and wool etc.), glass, metal, ceramics, or lather, by applying energy to the ink prepared by the aforementioned method.

When an image is formed, a fine polymer particle dispersion (or polymer latex) may be used in combination with the ink to impart gloss and water resistance, and improve weather resistance. The polymer latex may be applied to a recording medium before, after, or simultaneously with addition of a colorant. Therefore, the polymer latex may be added to a recording medium or ink, or alternatively, it may be applied singly in the form of a liquid.

Now, the recording medium (in particular, recording paper and recording film) for use in ink-jet recording using the ink of the present invention will be explained. The recording paper and recording film comprise a support or a base, which is generally made of chemical pulp such as LBKP, and NBKP, mechanical pulp such as GP, PGW, RMP, TMP, CTMP, CMP, and CGP, or used pulp such as DIP. To the pulp, if necessary, additives such as a pigment, binder, sizing agent, fixing agent, cationic agent, and paper strength reinforcing agent are added and made into paper, for example, by a Fourdrinier paper machine or a cylinder paper machine. The substrate thus produced may be used. Other than these supports, a synthetic paper and a plastic film sheet may be used. A support preferably has a thickness of 10 to 250 μm and a grammage of 10 to 250 g/m². To a support, an ink-receiving layer and a back-coat layer may be directly attached. Alternatively, the ink-receiving layer and back-coat layer may be provided after a size press and an anchor coat layer are attached by starch or polyvinyl alcohol. A support may be subjected to a flattening treatment performed by a calendar apparatus such as a machine calendar, TG calendar, and soft calendar. As the support, use may be herein preferably made of a paper sheet and plastic film having a laminate film of polyolefin (e.g., polyethylene, polystyrene, polyethylene terephthalate, polybutene and a copolymer of these) on both surfaces. It is preferable to add a white pigment (e.g., titanium oxide and zinc oxide) or a color imparting dye (e.g., cobalt blue, ultramarine blue, and neodymium oxide) to such a polyolefin.

To the ink-receiving layer to be formed on a support, a pigment and a hydrophilic binder may be contained. As such a pigment, a white pigment is preferable. Examples of the white pigment include inorganic white pigments such as calcium carbonate, kaolin, talc, clay, diatomite, synthetic amorphous silica, aluminum silicate, magnesium silicate, calcium silicate, aluminum hydroxide, alumina, lithopone, zeolite, barium sulfate, calcium sulfate, titanium dioxide, zinc sulfate, and zinc carbonate; and organic pigments such as styrene pigment, acrylic pigment, urea resin, and melamine resin. As a white pigment contained in the ink-receiving layer, porous inorganic pigments are preferable and synthetic amorphous silica having a large pore area is particularly preferable. As the synthetic amorphous silica, use may be made of both silicic acid anhydride obtained by a dry manufacturing method and hydrous silicic acid obtained by a wet manufacturing method. In particular, hydrous silicic acid is preferably used.

As the hydrophilic binder to be contained in the ink receiving layer, mention may be made of water soluble polymers such as polyvinyl alcohol, silanol modified polyvinyl alcohol, starch, cationic starch, casein, gelatin, carboxymethylcellulose, hydroxylethylcellulose, polyvinyl pyrrolidone, polyalkylene oxide, polyalkylene oxide derivative; and water dispersible polymers such as styrene-butadiene latex and acrylic emulsion. These hydrophilic binders may be used singly or in combination of two or more types. Of them, polyvinyl alcohol and silanol modified polyvinyl alcohol is preferable in the present invention in terms of adhesiveness to a pigment and anti-detachability of the ink-receiving layer. To the ink receiving layer, a mordant, anti-hydration agent, light fastness improver, surfactant, and other additives may be contained other than a pigment and aqueous binder.

As the mordant to be added to the ink-receiving layer, for example, a polymer mordant is used.

As the anti-hydration agent, which is effective to make an image to be resistant to water, a cationic resin is preferably used. Examples of the cationic resin include polyamide-polyamine-epichlorhydrin, polyethylene imine, polyamine sulfone, dimethyl diallyl ammonium chloride polymer, cationic polyacrylamide, and colloidal silica. Of these cations, polyamide-polyamine-epichlorhydrin is particularly preferable. The content of such a cationic resin is preferably 1 to 15% by mass based on the total solid matter of the ink-receiving layer, and particularly preferably 3 to 10% by mass.

Examples of the light fastness improver include UV absorbers such as zinc sulfate, zinc oxide, hindered amine type antioxidants, benzophenones, and benzotriazoles. Of them, zinc sulfate is preferable.

A surfactant serves as a coating auxiliary agent, detachability improver, slippage improver, or antistatic agent. In place of a surfactant, an organic fluoro compound may be used. Such an organic fluoro compound is preferably hydrophobic. Examples of the organic fluoro compound include fluorine surfactants, oily fluorine compounds (e.g., fluorine oil), and solid fluorine compounds (e.g., tetrafluoroethylene resin). As additives to be added to the ink-receiving layer, mention may be made of a pigment dispersion agent, thickening agent, antifoaming agent, dye, fluorescent whitening agent, antiseptic agent, pH adjuster, matting agent, and hardening agent. Note that the ink-receiving layer may be a single layer or a double layer.

To a recording sheet or recording film, a back coat layer may be provided. As an additive to be added to the back coating layer, mention may be made of a white pigment, hydrophilic binder and other components. Examples of the white pigment to be contained in the back coat layer include inorganic white pigments such as light calcium carbonate, heavy calcium carbonate, kaolin, talc, calcium sulfate, barium sulfate, titanium dioxide, zinc oxide, zinc sulfide, zinc carbonate, satin white, aluminum silicate, diatomite, calcium silicate, magnesium silicate, synthetic amorphous silica, colloidal silica, colloidal alumina, pseudoboehmite, aluminum hydroxide, alumina, lithopone, zeolite, hydrated halloysite, magnesium carbonate, and magnesium hydroxide; and organic pigments such as a styrene type plastic pigment, acrylic plastic pigment, polyethylene, microcapsules, urea resin, and melamine resin.

Examples of the hydrophilic binder to be contained in the back coat layer include water soluble polymers such as styrene/maleate salt copolymer, styrene/acrylate salt copolymer, polyvinyl alcohol, silanol modified polyvinyl alcohol, starch, cationic starch, casein, gelatin, carboxymethylcellulose, hydroxylethylcellulose, and polyvinyl pyrrolidone; and water dispersible polymers such as styrene-butadiene latex and acrylic emulsion. As other components to be contained in the back coat layer, mention may be made of an antifoaming agent, foam suppressor, dye, fluorescent whitener, antiseptic agent, and anti-hydration agent.

To the layers constituting an ink-jet recording sheet or recording film (including a back coat layer), polymer latex may be added. The polymer latex is used for improving film characteristics, more specifically, for stabilizing dimension, preventing curling, adhesion, and cracking. When polymer latex having a low glass transition temperature (40° C. or less) is added to a layer containing a mordant, cracking and curling of the layer can be prevented. Furthermore, when polymer latex having a high glass transition temperature is added to the back coat layer, curling can be also prevented.

Such a recording sheet and recording film are generally called ink-jet-specific paper, glossy paper or glossy film and commercially available as Pictorico (manufactured by Asahi Glass Co.); color BJ paper, high quality special-purpose paper, color BJ photo film sheet, super photo paper, professional photo paper (all manufactured by Cannon Inc.); color image jet paper (manufactured by Sharp Corporation); PM photo paper, super fine specific glossy paper (all manufactured by Epson Corporation), and Pictafine (manufactured by Hitachi Maxell K K). In particular, in the ink-jet recording method using the ink of the present invention, a recording sheet and recording film having an ink-receiving layer containing inorganic white pigment particles on a substrate, particularly effectively works as a recording medium. Needless to say, ordinary paper may also be used.

A colored body formed by using the ink of the present invention refers to the one printed and colored by ink-jet recording using the ink prepared by the aforementioned method.

When recording is made on a recording medium by the ink-jet recording method of the present invention, for example, an ink container containing the ink is set at a predetermined position of an ink-jet printer, and then, recording is performed in accordance with a general method. As such an ink-jet printer, mention may be made of a piezo printer using mechanical vibration and a bubble jet® printer using foams produced by heating.

The ink according to the present invention does not generate a precipitation or cause dissociation during storage. The ink according to the present invention, when it is used in an ink-jet printer, does not block an injector (or an ink head). The ink according to the present invention causes no physical change even if it is repeatedly circulated within a continuous ink-jet printer for a relatively long time, or even if it is intermittently used in an on-demand ink-jet printer.

The ink of the present invention is clear yellow having high chroma. When it is used in combination with other ink of magenta and cyan, the ink of the present invention can produce a wide range of color tone over the visible region. Furthermore, when it is used in combination with conventional magenta ink, cyan ink and black ink excellent in light fastness, water resistance, and moisture resistance, it is possible to obtain a printed matter excellent in light fastness, water resistance, and moisture resistance. Furthermore, ozone resistance of the ink of the present invention can be controllable in accordance with the resistant levels of other colors such as magenta, cyan, and black.

The yellow ink of the present invention is prepared by using the azo compound of the formula (12) or a salt thereof. The azo compound or a salt thereof may be used in the form of powder or in an aqueous dye solution that has been prepared by adding water, a water soluble organic solvent, and ink adjuster to a concentrated aqueous yellow dye solution previously prepared. Industrially, the latter method is generally employed.

The concentration of the concentrated aqueous dye solution is not particularly limited as long as ink containing a dye in a desired concentration can be prepared by adding an aqueous organic solvent and an ink adjuster to the dye solution; however it is generally 10% by mass or more and preferably 10 to 15% by mass.

Such an aqueous dye solution has good stability with time in the absence of a solubilizer such as urea and is stable further at low temperature without causing crystal precipitations or producing a viscosity gradient between the upper side and lower side of the aqueous solution. When urea is used as a solubilizer, the range of choice for an ink adjuster is limited and urea gradually decomposes during storage to generate carbon dioxide and ammonia, with the result that pH shifts to an alkaline side. Accordingly, ammonia odor is produced and air bubbles are generated. Because of these problems, using no urea as a solubilizer is a big advantage. The pH of the aqueous dye solution is preferably between 6 and 11 in consideration of ink preparation.

EXAMPLES

Now, embodiments of the present invention will be more specifically explained with reference to the following Examples, which should not be construed as limiting the invention. Note that the chemical structure of a compound in each step will be expressed in the form of a free acid. The term "parts" and "%" used herein is based on mass unless otherwise specified.

Example 1

(Synthesis)

The compound represented by a formula (7) was obtained by subjecting diazotized 4-nitro-4'-aminostilben-2,2-disulfonic acid and 3-aminonaphthalene-1-sulfonic acid to a coupling reaction, oxidizing, triazolizing, and reducing its nitro group in accordance with a known method. After 150.5 parts of the compound of the formula (7) was dissolved in 800 parts of water while adjusting pH with sodium carbonate to 6.0 to 8.0, 47.4 parts of a 40% aqueous sodium nitrite solution was added to the solution, which was then added dropwise to 78.2 parts of a 35% aqueous hydrochloric acid diluted with 600 parts of water. In this manner, diazotization was performed.

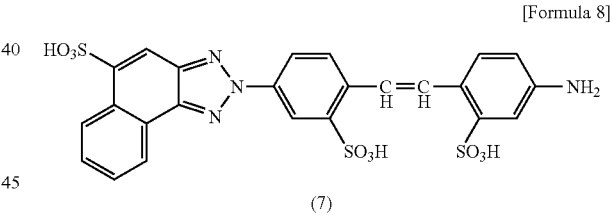

[Formula 8]

(7)

In 100 parts of water, 31.2 parts of sodium hydrogen sulfite was dissolved. To this solution, 30.0 parts of a 30% formalin solution was added, and then, 27.9 parts of aniline was added dropwise. After the dropwise addition, the temperature of the solution was increased to 50° C. and the solution was stirred for 3 hours at the same temperature and thereafter cooled to 5° C. The precipitated crystal was filtered and dried to obtain a compound represented by the formula (8). Subsequently, 52.5 parts of the compound of the formula (8) was dissolved in 300 parts of water while adjusting pH with sodium carbonate to 7.0 to 8.0. To the resultant solution, a suspension of the diazotized compound obtained in the aforementioned reaction was added dropwise at room temperature while maintaining pH at 7.0 to 8.0 with addition of sodium carbonate. The resultant mixture was stirred at room temperature for 5 hours while maintaining the same pH to obtain a solution containing the compound represented by the formula (9).

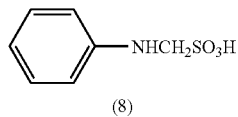

(8)

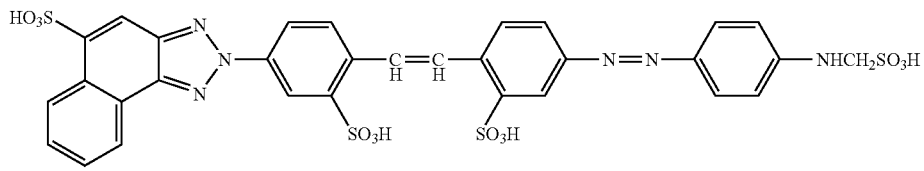

(9)

To the solution obtained above, 1000 parts of water was added and thereafter heated to 75° C. The pH value of the resultant solution was adjusted to 11.5 with adding sodium hydroxide. The mixture was stirred at the same temperature for 4 hours while maintaining the pH value within the range of 11.0 to 11.5 with addition of sodium hydroxide. Thereafter, hydrochloric acid was added to adjust the pH of the solution to 9.0 and then sodium chloride was added to obtain a precipitate. The precipitate was filtered to obtain 117.5 parts of the compound of the formula (10).

resultant solution was added dropwise to a solution formed by diluting 100.4 parts of a 35% hydrochloric acid solution with 700 parts of water to perform a diazotization reaction. To this suspension, a suspension formed by 37.0 parts of 6-aminonaphthalene-2-sulfonic acid in 120 parts of water was added and stirred for one hour while maintaining the pH value within the range of 4.6 to 5.2 by addition of sodium carbonate. Thereafter, the pH value was adjusted to 7.0 to 8.0 by addition

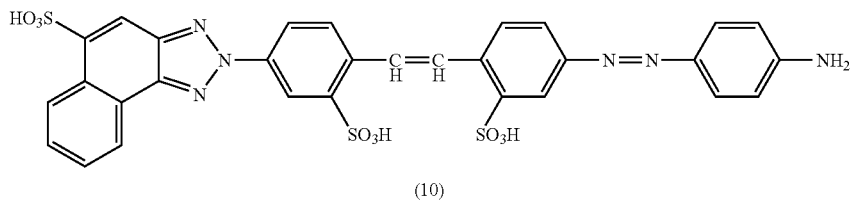

(10)

After the compound of the formula (10) obtained above was dissolved in 3,500 parts of water, 40.0 parts of a 40% aqueous sodium nitrite solution was added thereto. The of sodium carbonate, then sodium chloride was added to obtain a precipitate, which was filtered to obtain 140.6 parts of the compound of the formula (11).

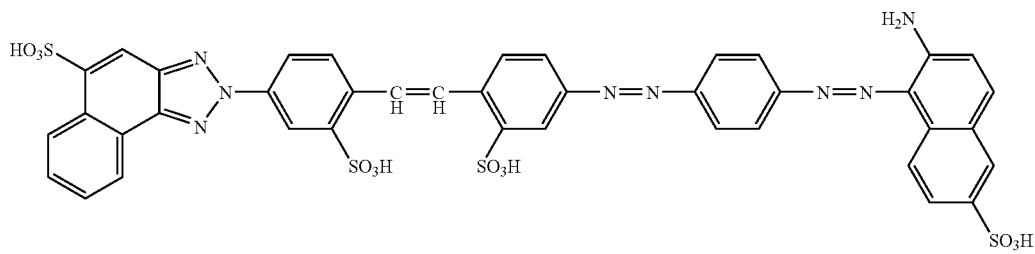

(11)

The compound of the formula (11) obtained above was dissolved in 3,000 parts of water and the temperature of the resultant solution was increased to 60° C. and its pH value was adjusted to 11.5 by addition of sodium hydroxide. To this solution, 240 parts of a 12% aqueous sodium hypochlorite solution was added and the temperature of the resultant solution was increased to 70° C. After the solution was stirred for one hour at 70° C., 35% hydrochloric acid was added to adjust pH to 8.0. Sodium chloride was then added to the solution to obtain a precipitate, and the solution was filtered to obtain a cake. The obtained cake was dissolved in 1,500 parts of water and crystallized with addition of 1000 parts of 2-propanol. The crystals were filtered, and dried to obtain 100.5 parts of the compound of the formula (12).

The maximum absorption wavelength (λmax) of the compound in water was 404 nm.

The content of metal ions:

According to ICP emission spectroscopic analysis, copper ion was 10 ppm or less, calcium 160 ppm, magnesium 100 ppm, aluminum 10 ppm or less, iron 10 ppm or less and silica 10 ppm or less.

The content of anions:

According to ion chromatography, chlorine ions were 380 ppm, and sulfate ions 400 ppm.

compound described in Example 1 of Patent document 1 as Comparative Example 3, while adjusting pH to 9 with sodium hydroxide. The obtained aqueous dye solutions were allowed to stand still at 0° C. and 15° C. The results are shown in Table 1.

TABLE 1

|  | Standing still at 0° C. | Standing still at 15° C. |
|---|---|---|
| Example 1 | After one month, no precipitate was observed | After one month, no precipitate was observed |
| Comparative Example 1 | After 20 days, precipitate was observed | After one month, no precipitate was observed |
| Comparative Example 2 | After 3 days, precipitate was observed | After 7 days, precipitate was observed |
| Comparative Example 3 | After 3 days, precipitate was observed | After 7 days, precipitate was observed |

From the results of Table 1, a precipitate and foreign matter were generated when the aqueous dye solutions of Comparative Example 1 to 3 were allowed to stand still at 0 to 15° C. Therefore, the storage stability thereof was low. However, no precipitate and foreign matter were generated in the case of the aqueous dye solution using the azo compound of the

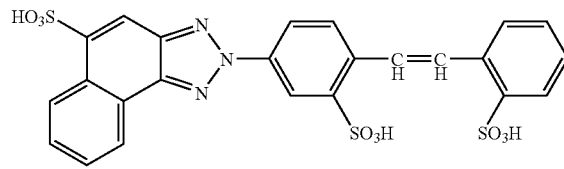

[Formula 12]

(12)

Reference Example

A dye represented by the general formula (3) was synthesized in accordance with the method described in Example 1 of Patent document 3. The obtained compound was desalted by a reverse osmotic membrane to reduce the content of inorganic substances. The compound thus obtained is represented by the general formula (3) where $M^3$ was sodium. As a dye represented by the general formula (2), use was made of KST Yellow J-GX (manufactured by Nippon Kayaku Co., Ltd.) where $M^2$ of the general formula (2) was sodium. As a dye represented by the general formula (4), use was made of KST Yellow J-005 (manufactured by Nippon Kayaku Co., Ltd.) where $M^4$ of the general formula (4) was sodium. Both dyes were desalted by a reverse osmotic membrane to reduce the content of inorganic compounds.

Example 2

(Test for Storage Stability)

The compound represented by the formula (12) and synthesized in Example 1 was used to prepare a 10% aqueous dye solution while adjusting pH to 9 with sodium hydroxide.

As comparative examples, 10% aqueous dye solutions were prepared using a compound (Na salt) of the general formula (2) as Comparative Example 1, a compound (Na salt) of the general formula (3) as Comparative Example 2, and a formula (12) reduced in content of copper ions according to Example 1, when it was allowed to stand still at 0 to 15° C. Thus, it was demonstrated that it is stable for a long time.

Example 3

(Preparation of Ink Composition and Test Examples)

(A) Preparation of Ink

Liquids with the following compositions were prepared and filtered through a 0.45 μm membrane filter to obtain aqueous ink compositions for ink-jet recording. The water used herein was ion exchanged water. Note that water and sodium hydroxide were added so as to obtain 100 parts of the ink compositions at pH of 8 to 10.

The ink samples were prepared having dye compositions in ratios of (a) to (f) shown in Table 2 below such that the total mass amount of dye components in ink came to 2.0 parts. An ink sample having a dye composition (a) was designated Ink (a). Ink samples (b) to (f) were designated in the same manner. The compositions of the ink samples are shown in Table 3.

TABLE 2

| Composition of dye components |  |
|---|---|
| (a) | Only the compound of the formula (12) obtained in Example 1 |
| (b) | The compound of the formula (12):the compound (Na salt) of the formula (3) = 4:1 |

TABLE 2-continued

Composition of dye components (c) The compound of the formula (12):the compound (Na salt) of the formula (3) = 1:1
(d) The compound of the formula (12):the compound (Na salt) of the formula (3) = 1:4
(e) The compound of the formula (12):the compound (Na salt) of the formula (3): the compound (Na salt) of the formula (4) = 5:3:2
(f) The compound of the formula (12):the compound (Na salt) of the formula (2) = 4:1

TABLE 3

| | |
|---|---|
| Dye component shown in Table 2 (in terms of solid matter) | 2.0 parts |
| Water and caustic soda | 78.9 parts |
| Glycerol | 5.0 parts |
| Urea | 5.0 parts |
| N-methyl-2-pyrrolidone | 4.0 parts |
| IPA | 3.0 parts |
| Butylcarbitol | 2.0 parts |
| Sarfinol 104PG50 (Surfactant, Nissin Chemical Industry Co., Ltd.) | 0.1 part |
| Total | 100.0 parts |

(B) Ink-Jet Printing

Using an ink-jet printer (BJ S630, manufactured by Canon Inc.), ink-jet recording was made on two recording mediums namely, glossy paper A (professional photo paper PR-101, manufactured by Canon Inc.) and glossy paper B (PM photo paper KA420PSK, manufactured by Epson Corporation). Recorded images of aqueous yellow ink compositions according to the present invention were checked for hue, clarity, light fastness, ozone resistance and moisture resistance. The results are shown in Table 4.

As comparative examples, ink compositions were prepared in the same manner as above by using the dye (Na salt) of the formula (2) and the dye (Na salt) of the formula (3) and designated as Ink H-(2) and Ink H-(3), respectively. They were evaluated for hue, clarity, light fastness, ozone resistance and moisture resistance. The results are shown in Table 4.

(C) Method for Evaluating Recorded Image

1. Hue Evaluation

The hue and clarity of a recorded image:

The recorded paper was measured for color by Gretag, Macbeth Spectro Eye (manufactured by GRETAG). Values $L^*$, $a^*$ and $b^*$ were calculated with respect to patterns having a reflection density (D value) within 1.15 to 1.36.

2. Light Fastness Test

Test pieces of the recorded images were irradiated with a xenon weather meter (Type Ci4000 manufactured by ATLAS) at an illuminance of 0.36 W/m², a vessel temperature of 24° C. and a humidity of 60% RH for 50 hours. The reflection density (D value) of each of the test pieces was measured before and after the test by a color measurement system within the range of a reflection density of 1.15 to 1.36. After the measurement, a dye residual ratio was calculated in accordance with the equation:

(The reflection density after test/The reflection density before test)×100(%).

3. Ozone Resistance Test

Test pieces of recorded images were allowed to stand alone in an ozone weather meter (type: OMS-H, manufactured by Suga Test Instruments) at an ozone concentration of 12 ppm, a vessel temperature of 24° C., and a humidity of 60% RH, for 3 hours. After the test, the reflection density (D value) of each of the test pieces was measured before and after the test by a color measurement system within the range of a reflection density of 1.15 to 1.36. After the measurement, a color residual ratio was calculated in accordance with the equation:

(The reflection density after test/The reflection density before test)×100(%).

4. Moisture Resistance Test

The test pieces of recorded images were allowed to stand alone in a thermo-hygrostat (manufactured by Ohken. Co., Ltd.) at a vessel temperature of 50° C., and a humidity of 90% RH, for 3 days. After the test, bleeding of the test pieces was visually evaluated on a scale of three scores.

TABLE 4

| | Hue | | | Light fastness residual rate (%) | Ozone resistance residual rate (%) | Moisture resistance |
|---|---|---|---|---|---|---|
| | $L^*$ | $a^*$ | $b^*$ | | | |
| Ink (a) | | | | | | |
| Glossy paperA | 90.4 | −2.7 | 77.1 | 96.0% | 50.0% | G |
| Glossy paperB | 89.9 | −3.8 | 80.2 | 97.8% | 69.9% | G |
| Ink (b) | | | | | | |
| Glossy paperA | 91.0 | −3.7 | 73.3 | 94.4% | 59.5% | G |
| Glossy paperB | 90.3 | −5.1 | 78.1 | 96.3% | 72.8% | G |
| Ink (c) | | | | | | |
| Glossy paperA | 91.4 | −5.7 | 73.0 | 92.6% | 70.2% | G |
| Glossy paperB | 91.1 | −6.8 | 75.2 | 96.1% | 80.6% | G |
| Ink (d) | | | | | | |
| Glossy paperA | 92.0 | −7.1 | 68.5 | 91.4% | 79.3% | G |
| Glossy paperB | 91.4 | −8.6 | 70.6 | 92.6% | 88.5% | G |
| Ink (e) | | | | | | |
| Glossy paperA | 91.1 | −5.1 | 74.6 | 93.5% | 73.2% | G |
| Glossy paperB | 90.6 | −6.1 | 76.4 | 94.0% | 81.3% | G |
| Ink (f) | | | | | | |
| Glossy paperA | 90.7 | −3.7 | 76.9 | 94.0% | 58.0% | G |
| Glossy paperB | 90.2 | −4.9 | 79.8 | 95.8% | 71.8% | G |
| Ink H-(2) | | | | | | |
| Glossy paperA | 92.0 | −7.9 | 76.0 | 88.3% | 88.3% | G |
| Glossy paperB | 91.4 | −9.2 | 78.3 | 88.2% | 95.6% | B |
| Ink H-(3) | | | | | | |
| Glossy paperA | 92.5 | −8.7 | 68.4 | 90.4% | 87.0% | G |
| Glossy paperB | 92.1 | −9.5 | 67.4 | 92.4% | 96.6% | G |

Evaluation standards:
G: No bleeding was observed
M: Bleeding was slightly observed
B: Bleeding was significantly observed As is apparent from Table 4, Ink (a) prepared by using the Azo compound of the formula (12) of the present invention is extremely excellent in light fastness compared to Ink H-(2) and Ink H-(3) and equivalent or higher in moisture resistence. From the results of Ink (f), it is found that even if the compound of the formula (12) and the compound (2) are combined, moisture resistance is sastifactory. On the other hand, from the results of Ink (b) and Ink (c), it is found that ozone resistence can be controlled by changing the mixing rato of the compound of the formula (12) and a predetermined yellow dye. Furthermore, it was demonstrated that the aqueous ink of the present invention is a yellow dye having a good hue as well as high clarity and high chroma.

From the foregoing, when the compound synthesized by the method of the present invention is used, it is possible to produce very excellent yellow ink-jet recording ink having a wide variety of applications.

INDUSTRIAL APPLICABILITY

The azo compound reduced in copper-ion content according to the present invention is extremely excellent in water solubility. In addition, an aqueous dye solution, even if the concentration of the azo compound is relatively high (10% by mass), exhibits excellent storage stability. More specifically, even if the dye solution is allowed to stand still under very stringent conditions of a temperature of 0 to 15° C. for a long time, no precipitate and foreign matter are observed. The ink using the azo compound reduced in copper-ion content according to the present invention is free from crystal precipitation, physical change, and color change after a long-term storage. Hence, the ink is excellent in storage stability. Furthermore, the ink according to the present invention has a feature in that it is easily filtered by a membrane filter in the manufacturing of the ink. Thus, it is possible to produce ink-jet recording ink containing dye in a high concentration. Furthermore, the color value is high. The printed matter obtained by using ink-jet recording ink containing the ink of the present invention as yellow ink is excellent in light fastness, ozone resistance, and moisture resistance. When the ink of the present invention is used in combination with magenta, cyan and black dyes, it is possible to realize ink-jet printing excellent in light fastness, ozone resistance and moisture resistance. Furthermore, when the ink of the present invention is used in combination with another type of yellow dye, it is possible to control of degree of discoloration. Moreover, since the printing surface is suitable for the hue of yellow and clear, if the ink of the present invention is used in combination with other ink colors such as magenta and cyan, a wide range of color tone over the visible region can be produced. Hence, the ink of the present invention is extremely useful as yellow ink-jet recording ink.

The invention claimed is:

1. An azo compound represented by the following formula (12) having a content of copper ions as impurity of 100 ppm or less, or a salt thereof

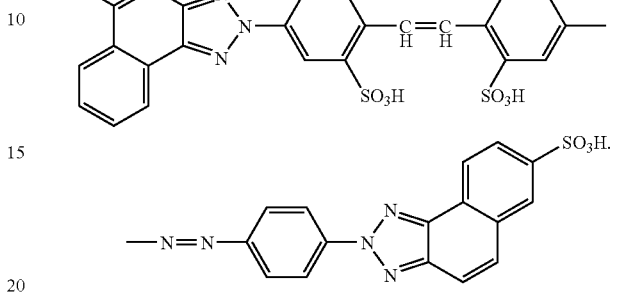

(12)

2. An aqueous dye solution comprising the azo compound represented by the formula (12) or a salt thereof according to claim 1 in an amount of 10% by mass or more and having pH of 6 to 11.

3. The aqueous dye solution according to claim 2, wherein the content of inorganic anions is 1% by mass or less.

4. Ink charactorizod by comprising the azo compound represented by the formula (12) or a salt thereof according to claim 1 as a dye component.

5. Ink comprising the azo compound represented by the formula (12) or a salt thereof according to claim 1 and an azo yellow dye (B).

6. The ink according to claim 5, wherein the azo yellow dye (B) is a compound represented by the following general formula (2), (3) or (4):

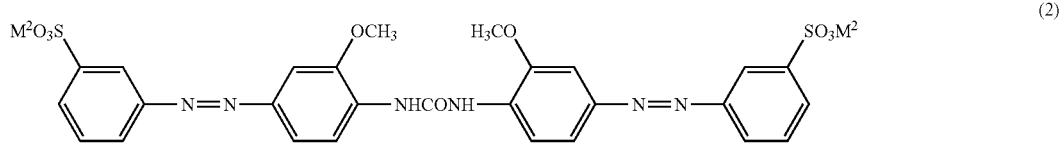

(2)

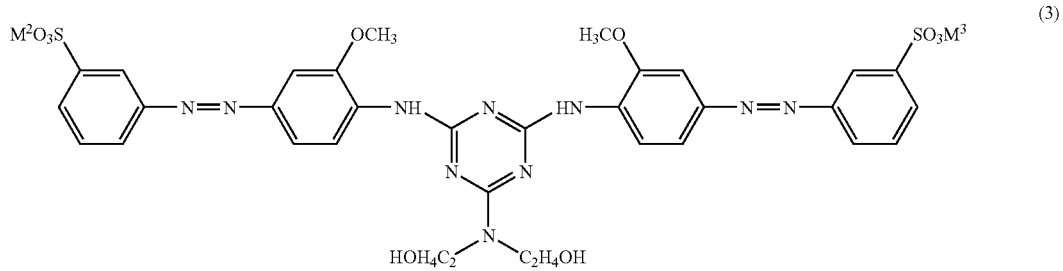

(3)

-continued

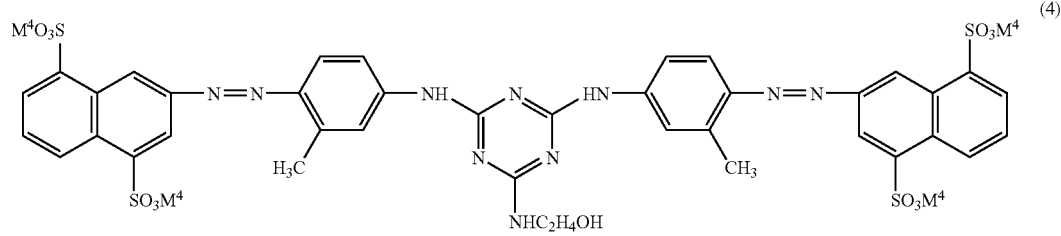

wherein $M^2$ to $M^4$ each independently represent a hydrogen atom, alkali metal, alkaline earth metal, cation of an organic amine, or ammonium ion.

7. The ink according to claim 6, wherein the azo yellow dye (B) is composed of not less than two compounds represented by the general formulas (2) to (4).

8. The ink according to claim 4 or 5, comprising water and a watersoluble organic solvent.

9. The ink according to claim 4 or 5 for ink-jet recording.

10. An ink set comprising the ink according to claim 4 or 5 as yellow ink, at least one water-soluble anthrapyridone dye as magenta ink, and at least one watersoluble copper phthalocyanine dye as cyan ink.

11. An ink-jet recording method for recording an image on a recording medium comprising ejecting ink droplets in response to recording signals, wherein the ink comprises the ink according to claim 4 or 5.

12. The ink-jet recording method according to claim 11, wherein the recording medium is an information transmission sheet.

13. The ink-jet recording method according to claim 12, wherein the information transmission sheet is a surface-coated sheet and has an ink-image receiving layer containing white inorganic pigment particles on a substrate.

14. An ink container comprising the ink according to claim 4 or 5.

15. An ink-jet printer comprising the ink container according to claim 14.

16. A colored body being colored by the ink according to claim 4 or 5.

* * * * *